United States Patent [19]

Figlhuber et al.

[11] 4,291,579

[45] Sep. 29, 1981

[54] INSPECTION DEVICE

[75] Inventors: Dietgar Figlhuber; Johannes Gallwas, both of Erlangen; Robert Weber, Uttenreuth; Jakob Weber, Erlangen, all of Fed. Rep. of Germany

[73] Assignee: Kraftwerk Union Aktiengesellschaft, Mulheim an der Ruhr, Fed. Rep. of Germany

[21] Appl. No.: 58,423

[22] Filed: Jul. 18, 1979

[30] Foreign Application Priority Data

Aug. 3, 1978 [DE] Fed. Rep. of Germany ....... 2834108

[51] Int. Cl.³ .......................................... G01N 29/04
[52] U.S. Cl. ...................................... 73/636; 73/637; 73/638
[58] Field of Search ................. 73/635, 636, 637, 638, 73/640, 622, 623, 635

[56] References Cited

U.S. PATENT DOCUMENTS 3,987,666 10/1976 Blanc et al. ........................... 73/623
4,131,018 12/1978 Müller et al. ......................... 73/637

Primary Examiner—Anthony V. Ciarlante
Attorney, Agent, or Firm—Herbert L. Lerner

[57] ABSTRACT

Inspection device for testing vessels surrounded by a wall having an inner and an outer surface including a movable testing device and a track for guiding the testing device. The guiding track extending from a portion disposed in the vicinity of the vessel between the wall and the vessel, through a U-shaped portion over the wall and ending at a rest position for the testing device on the outer surface of the wall.

8 Claims, 4 Drawing Figures

INSPECTION DEVICE

The invention relates to an inspection device for the testing of vessels with a track which is disposed in the vicinity of the vessel, between the latter and a wall surrounding the vessel. The track serves for guiding a movable testing device along the vessel and into a rest position which is located on the side of the wall facing away from the vessel. Such inspection devices are required particularly for reactor pressure vessels of nuclear reactors, the reliability of which must be guaranteed with the highest degree of confidence.

It is an object of the invention to make use of the wall to the fullest extent with respect to its shielding function, which is important particularly in nuclear plants.

With the foregoing and other objects in view, there is provided, in accordance with the invention, an inspection device for testing vessels surrounded by a wall having an inner and an outer surface comprising a movable testing device and a track for guiding the testing device, the guiding track extending from a portion disposed in the vicinity of the vessel between the wall and the vessel, through a U-shaped portion passing over the wall and ending at a rest position for the testing device on the outer surface of the wall.

The advantage of this construction is that the wall can fulfill its intended function, as desired. In addition, the space required in the radial direction, relative to the axis of the vessel and the wall, is relatively small. Surprisingly, it has also been found that relatively tight curves can be negotiated with the U-shaped track construction without difficulties resulting in guiding the testing device. This is true even when the axis of the vessel is vertical, so that the U-shaped track part, provided according to the invention for moving the testing device, has a vertically ascending and a vertically descending branch. However, the bending radii of the track according to the invention should be at least two times the track thickness. It is further advisable to place the devices such as racks, which serve to move the testing device along the track, in such a manner that they are not deformed by the curvature of the track.

In accordance with another feature of the invention, there is provided a plurality of additional guiding tracks disposed alongside the first-mentioned guiding track, each having U-shaped portions, and means disposed at the end of the guiding tracks for coupling the guiding tracks together for common usage by the testing device. It is therefore possible to examine large vessels with a single testing device, which is led sequentially along, adjacent the wall of the generally cylindrical vessel. The tracks with their bends can extend in star-fashion relative to the axis of the cylinder. On the other hand, it is also conceivable for the testing device to be led from the U-shaped end of one track around the entire vessel to a U-shaped end on the opposite side, where a transfer to an adjacent coupling point can then be made.

In accordance with another feature of the invention, there are provided means for transporting the common testing device from coupling means to coupling means, transverse to the U-shaped portions.

In accordance with an added feature of the invention, the transporting means includes a transport track disposed transversely to the U-shaped portions and a carriage movable along the transport track. In view of the possibility of using the wall surrounding the vessel as the supporting device for the U-shaped bends, for the coupling means and for the transporting means running transversely thereto, in accordance with an additional feature of the invention, the transport track includes a carrying track and a support track, both being fixed to the outer surface of the wall. However, a horizontal floor enclosing the wall can also be used as the track, with which no direct anchoring of the carriage to the wall is necessary.

The invention is not limited to the requirement that the U-shaped bends which serve for guiding a common testing device, be equal.

Rather, in accordance with yet another feature of the invention, several of the U-shaped portions have different bending widths or bending radii, and there is provided a carriage connectible to the common testing device and means for transporting the carriage in direction parallel to a U-shaped portion or transversely thereto. In this manner, the movement of the carriage can be predetermined by tracks in both directions mentioned. In addition, it is also possible to provide only a support plane in the form of a horizontal floor and to leave it to the operating personnel to control the movements of the carriage on this support plane.

In accordance with yet a further feature of the invention, part of the guiding track is detachable, preferably in the vicinity of the U-shaped portion thereof.

Other features which are considered as characteristic for the invention are set forth in the appended claims.

Although the invention is illustrated and described herein as embodied in inspection device, it is nevertheless not intended to be limited to the details shown, since various modification and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
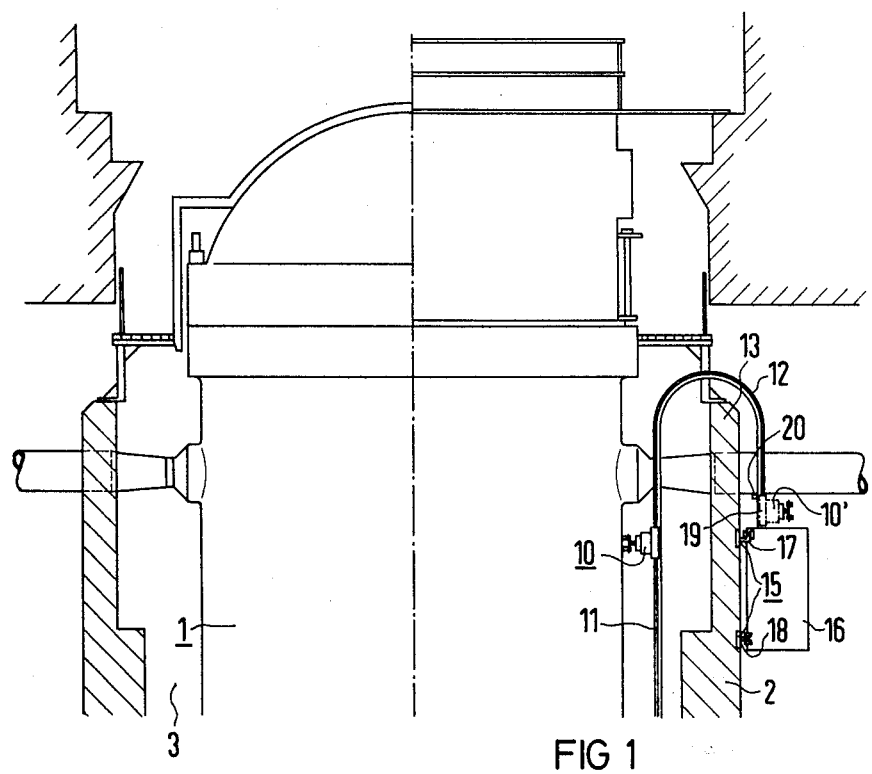
FIG. 1 is a fragmentary cross-sectional view of a first embodiment of an inspection device employed in a reactor pressure vessel of a boiling water nuclear power plant, in accordance with the invention.
Figure 2:
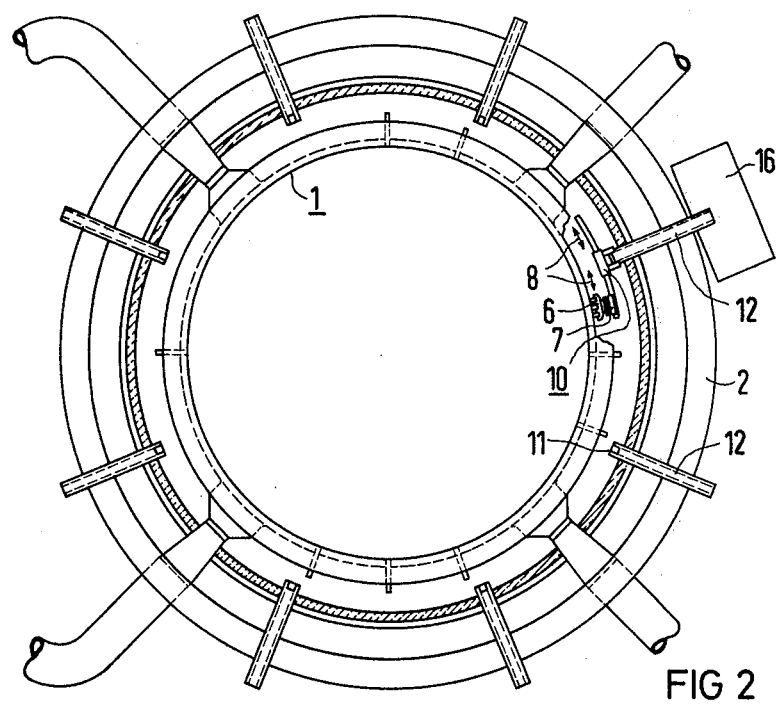
FIG. 2 is a top plan view of FIG. 1.

Referring now to the figures of the drawing and first, particularly, to FIGS. 1 and 2, there is seen a reactor pressure vessel 1 which is a thick-walled cylindrical steel vessel with a diameter of, for instance, 7 m. For shielding-off the radiation of the non-illustrated reactor core, the reactor pressure vessel 1 is completely enclosed by a cylindrical concrete wall 2, the thickness of which is about 1 m or more. The wall 2 surrounds the reactor pressure vessel 1 with a certain amount of spacing, so that a gap 3 is created. This gap is used for so-called in-service tests, i.e. for repetitive inspections of the reactor pressure vessel, with a testing device and especially with ultrasonic test heads.

The ultrasonic test heads are designated with reference numeral 6. They are mounted in multiple installation at a carrier 7 and can be moved in the horizontal direction as indicated by arrows 8 in FIG. 2. The test heads 6 can also be moved in the vertical direction of the cylindrical vessel 1. The device 10 serving this purpose is designated as a whole as a testing device. The testing device 10 is guided by guide tracks 11 which follow the vertical wall of the cylindrical pressure vessel; in the embodiment example according to FIG. 2, they are provided at eight equally spaced points of the pressure vessel 1.

At their upper end, these guide tracks 11 carry U-shaped bends 12 which are brought over the upper edge 13 of the wall 2, as shown in FIG. 1. As can be seen clearly in FIG. 1, the testing device 10 can therefore be brought from the test position facing the vessel 1, past the upper edge 13, into the rest position 10', shown in phantom by broken lines. In this position, the testing device is shielded from radiation by the wall 2. In the rest position 10', the testing device can be operated and serviced, if necessary.

In the embodiment example according to FIG. 1, the wall 2 supports a two-part transport track 15 for a supply carriage 16, which is associated with the testing device. The supply carriage 16 can contain, for instance, measuring lines and evaluation devices such as measured-data converters. It can further comprise propulsion devices for moving the testing device 10 by remote control.

The track 15 extends on the outside of the wall 2 around the circumference of the latter. It includes a carrying rail 17 and a support rail 18. The rollers of the supply carriage 16 cooperate with both parts of the track 15. Therefore, the supply carriage 16 can be moved with little effort transversely to the plane of the bends 12 of the guide track 11. The testing device 10 is moved by the track section 19, which supports the testing device 10 in the rest position 10', from one bend 12 to the next, where a connection can be established through coupling points 20.

Figure 3:
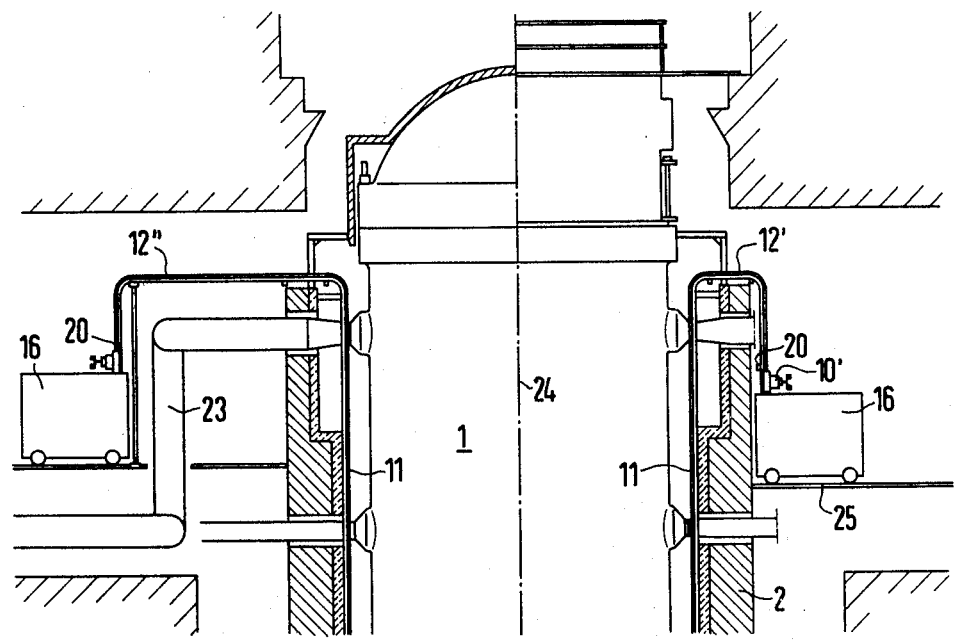
FIG. 3 is a view similar to FIG. 1, but showing a second embodiment of the invention.
Figure 4:
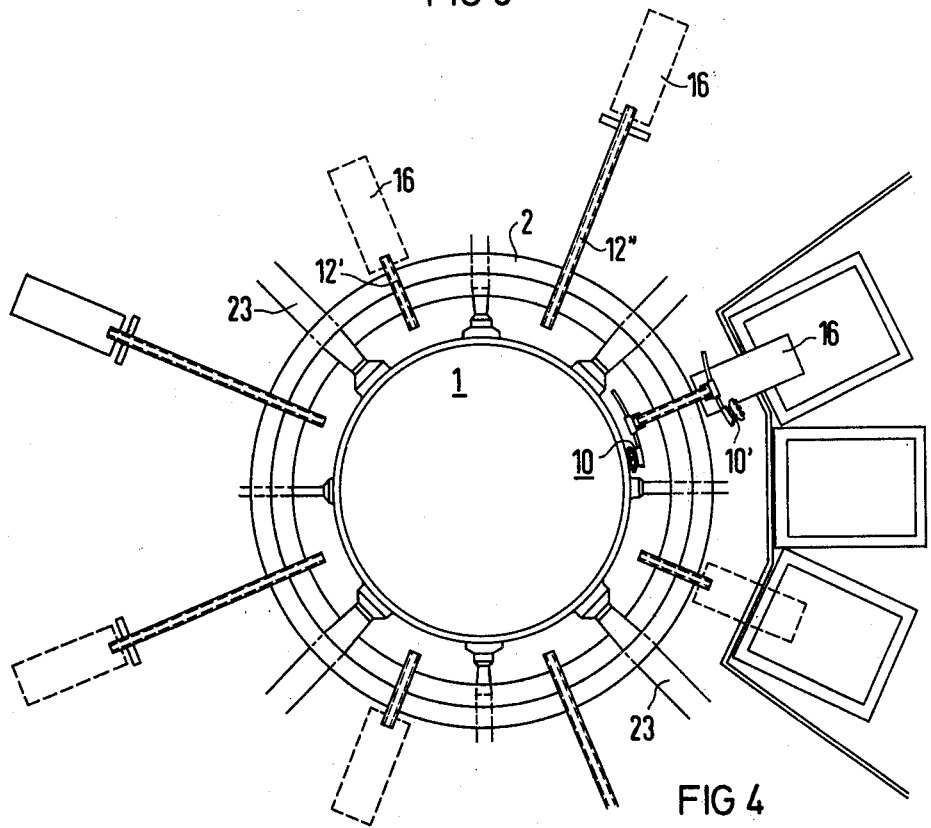
FIG. 4 is a top plan view of FIG. 3.

In the embodiment example according to FIGS. 3 and 4, different U-shaped bends 12' and 12" are associated with the tracks 11, so that the steam pipes 23 on the side of the wall 2 facing away from the pressure vessel 1 can be spanned. The coupling points 20 for the testing device 10, which in its rest position again is placed on a supply carriage 16, are therefore no longer disposed on a circular arc about the vertical axis 24, but are offset therefrom in the radial direction. In this embodiment, an intermediate floor 25, on which the carriage 16 can be moved in the plane of the bends 12' and 12" as well as transversely thereto, serves as the running surface for the carriage 16.

A section of the track 11 may be detachable by providing a conventional fastening device at any point along the track. It is particularly advantageous, however, if the detachable part is in the vicinity of the U-shaped bend.

There is claimed:

1. Inspection device for testing vessels surrounded by a wall having an inner and an outer surface comprising a movable testing device and a track for guiding said testing device, said guiding track extending from a portion disposed in the vicinity of the vessel between the wall and the vessel, through a U-shaped portion passing over the wall and ending at a rest position for said testing device on the outer surface of the wall.

2. Inspection device according to claim 1, including a plurality of additional guiding tracks disposed alongside said first-mentioned guiding track, each having U-shaped portions, and means for coupling said guiding tracks together for common usage by said testing device.

3. Inspection device according to claim 2, including means for transporting said common testing device from coupling means to coupling means, transverse to said U-shaped portions.

4. Inspection device according to claim 3, wherein said transporting means includes a transport track disposed transversely to said U-shaped portions and a carriage movable along said transport track.

5. Inspection device according to claim 4, wherein said transport track includes a carrying track and a support track, both being fixed to the outer surface of the wall.

6. Inspection device according to claim 2, wherein several of said U-shaped portions have different bending widths, and including a carriage connectible to said common testing device and means for transporting said carriage in direction parallel to a U-shaped portion and transversely thereto.

7. Inspection device according to claims 1, 2, 3, 4, 5 or 6, wherein part of said guiding track is detachable.

8. Inspection device according to claim 7, wherein said detachable part of said guiding track is in the vicinity of the U-shaped portion thereof.

* * * * *